US008801847B2

(12) United States Patent
Tuason et al.

(10) Patent No.: US 8,801,847 B2
(45) Date of Patent: *Aug. 12, 2014

(54) MICROCRYSTALLINE CELLULOSE COMPOSITIONS

(75) Inventors: Domingo C. Tuason, Bensalem, PA (US); Jose Amundarain, Burlington, NJ (US); Gregory R. Krawczyk, Princeton Junction, NJ (US); Edward Selinger, Langhorne, PA (US); William R. Blakemore, Topsham, ME (US); James J. Modliszewski, Brick, NJ (US); Joseph Lee, Warrington, PA (US); Frank Messick, Newark, DE (US)

(73) Assignee: FMC Corporation, Philadelphia, PA (US)

( * ) Notice: Subject to any disclaimer, the term of this patent is extended or adjusted under 35 U.S.C. 154(b) by 110 days.

This patent is subject to a terminal disclaimer.

(21) Appl. No.: 12/972,697

(22) Filed: Dec. 20, 2010

(65) Prior Publication Data

US 2011/0135798 A1 Jun. 9, 2011

Related U.S. Application Data

(63) Continuation of application No. 12/265,970, filed on Nov. 6, 2008, now Pat. No. 7,871,468, which is a continuation of application No. 10/513,530, filed as application No. PCT/US03/15146 on May 14, 2003, now Pat. No. 7,462,232.

(60) Provisional application No. 60/380,398, filed on May 14, 2002.

(51) Int. Cl.
| C08L 1/02 | (2006.01) |
| C08L 1/26 | (2006.01) |
| C08L 1/28 | (2006.01) |
| C08L 5/00 | (2006.01) |
| C08L 1/04 | (2006.01) |
| C08L 5/04 | (2006.01) |
| C08L 5/06 | (2006.01) |

(52) U.S. Cl.
CPC ... *C08L 1/04* (2013.01); *C08L 5/00* (2013.01); *C08L 5/04* (2013.01); *C08L 5/06* (2013.01)
USPC .................... 106/162.8; 106/162.9

(58) Field of Classification Search
USPC ............................ 106/162.8, 162.9
See application file for complete search history.

(56) References Cited

U.S. PATENT DOCUMENTS

| 3,145,146 | A |   | 8/1964  | Lieberman et al. |
| 3,146,168 | A |   | 8/1964  | Battista |
| 3,539,365 | A |   | 11/1970 | Durand et al. |
| 3,573,058 | A | * | 3/1971  | Tiemstra ............... 426/658 |
| 3,639,169 | A |   | 2/1972  | Broeg et al. |
| 4,017,598 | A |   | 4/1977  | Ohno et al. |
| 4,110,476 | A |   | 8/1978  | Rhodes |
| 4,263,334 | A |   | 4/1981  | McGinley |
| 4,264,637 | A |   | 4/1981  | Braverman |
| 4,426,518 | A |   | 1/1984  | Omiya |
| 4,693,750 | A |   | 9/1987  | Bauer et al. |
| 4,744,987 | A |   | 5/1988  | Mehra et al. |
| 4,980,193 | A |   | 12/1990 | Tuason et al. |
| 5,082,684 | A |   | 1/1992  | Fung |
| 5,192,569 | A |   | 3/1993  | McGinley et al. |
| 5,272,137 | A |   | 12/1993 | Blasé et al. |
| 5,286,510 | A |   | 2/1994  | Bauer et al. |
| 5,366,742 | A | * | 11/1994 | Tuason et al. ............... 426/96 |
| 5,409,907 | A |   | 4/1995  | Blase et al. |
| 5,415,804 | A |   | 5/1995  | Minami et al. |
| 5,505,982 | A |   | 4/1996  | Krawczyk et al. |
| 5,573,777 | A |   | 11/1996 | Serpelloni et al. |
| 5,605,712 | A |   | 2/1997  | Bertrand et al. |
| 5,607,716 | A |   | 3/1997  | Doherty et al. |
| 5,609,898 | A |   | 3/1997  | Kaji et al. |
| 5,709,896 | A |   | 1/1998  | Hartigan et al. |
| 5,725,886 | A |   | 3/1998  | Erkoboni et al. |
| 5,747,067 | A |   | 5/1998  | Auguello et al. |
| 5,769,934 | A |   | 6/1998  | Ha et al. |
| 5,789,004 | A |   | 8/1998  | Hogan et al. |
| 5,866,166 | A |   | 2/1999  | Staniforth et al. |
| 6,010,734 | A |   | 1/2000  | Whelan et al. |

(Continued)

FOREIGN PATENT DOCUMENTS

| EP | 1226818 A1 | 7/2002 |
| GB | 1010477    | 11/1965 |

(Continued)

OTHER PUBLICATIONS

Mitchell, S.A., et al., 'A Compaction Process to enhance dissolution of poorly water-soluble drugs using hydroxypropyl methylcellulose'. International Journal of Pharmaceutics, 250, pp. 3-11, 2003.
Kleinebudde, P., 'Roll Compaction/Dry Granulation: Pharmaceutical Applications'. European Journal of Pharmaceutics and biopharmaceutics, 58, pp. 317-326, 2004.
Deyampert Rogers, Tracey L., 'Content Considerations for Low Dosage Drug Formulations Processed by Roller Compaction'. Ph.D. Thesis, Purdue University, Aug. 1997.
Deyampert Rogers, Tracey L., 'Oral Preliminary Examination', Sep. 1, 1995.
Falzone, Angela Marie, 'Roller Compaction of Pharmaceutical Excipients and Excipient-drug Blends'. Ph.D. Thesis, Purdue University, Dec. 1990.
Skinner, G.W., 'The Evaluation of Fine-particle Hydroxyprpycellulose as a Roller Compaction binder in Pharmaceutical Applications'. Drug Development & Indust. Pharm, 25(10), pp. 1121-1128, 1999.

(Continued)

*Primary Examiner* — David M Brunsman
(74) *Attorney, Agent, or Firm* — FMC Corporation

(57) ABSTRACT

Ultra-fine microcrystalline cellulose compositions are disclosed which comprise co-attrited microcrystalline cellulose and a hydrocolloid. The compositions have a mean particle size of less than 10 microns. The compositions are prepared by subjecting a high solids mixture of microcrystalline cellulose and a hydrocolloid to high shear forces in the presence of an anti slip agent preferably an aqueous solution of an inorganic salt. The compositions are especially useful in food, pharmaceutical and cosmetic and industrial applications.

7 Claims, No Drawings

(56) References Cited

U.S. PATENT DOCUMENTS

| | | | |
|---|---|---|---|
| 6,025,007 A | | 2/2000 | Krawczyk |
| 6,037,380 A | * | 3/2000 | Venables et al. ............... 514/781 |
| 6,079,630 A | | 6/2000 | Schroeder |
| 6,106,865 A | | 8/2000 | Staniforth et al. |
| 6,117,474 A | | 9/2000 | Kamada et al. |
| 6,235,947 B1 | | 5/2001 | Yoshinari et al. |
| 6,254,905 B1 | | 7/2001 | Hojo et al. |
| 6,264,981 B1 | | 7/2001 | Zhang et al. |
| 6,270,830 B1 | | 8/2001 | Kamada et al. |
| 6,368,649 B1 | | 4/2002 | Van Bommel |
| 6,391,368 B1 | * | 5/2002 | Tuason et al. ................. 426/578 |
| 6,432,448 B1 | | 8/2002 | Augello et al. |
| 6,440,474 B1 | | 8/2002 | Buliga et al. |
| 6,475,539 B1 | | 11/2002 | Dewille et al. |
| 6,500,462 B1 | | 12/2002 | Augello et al. |
| 6,503,918 B2 | | 1/2003 | Yoshinari et al. |
| 6,517,871 B1 | | 2/2003 | Venkatesh et al. |
| 6,548,093 B1 | | 4/2003 | Collinge et al. |
| 6,689,405 B1 | * | 2/2004 | Tuason et al. ................... 426/93 |
| 6,709,713 B2 | | 3/2004 | Augello et al. |
| 6,723,342 B1 | | 4/2004 | Augello et al. |
| 6,726,949 B2 | | 4/2004 | Adolphi et al. |
| 6,752,939 B2 | | 6/2004 | Gereg |
| 6,753,017 B2 | | 6/2004 | Berkulin et al. |
| 6,936,277 B2 | | 8/2005 | Staniforth et al. |
| 6,936,628 B2 | | 8/2005 | Lee |
| 2,978,446 A1 | | 4/2008 | Battista et al. |
| 7,462,232 B2 | * | 12/2008 | Tuason et al. ............... 106/162.9 |
| 7,871,468 B2 | * | 1/2011 | Tuason et al. ............... 106/162.9 |
| 7,879,382 B2 | * | 2/2011 | Tuason et al. ................. 426/573 |
| 2003/0017204 A1 | | 1/2003 | Augello et al. |
| 2003/0129238 A1 | | 7/2003 | Augello et al. |
| 2004/0071821 A1 | | 4/2004 | Ashourian et al. |
| 2004/0121006 A1 | | 6/2004 | Narita et al. |
| 2004/0137043 A1 | | 7/2004 | Augello et al. |
| 2004/0185161 A1 | | 9/2004 | Ashourian et al. |
| 2004/0258827 A1 | | 12/2004 | Shen |
| 2005/0147710 A1 | | 7/2005 | Teckoe et al. |
| 2005/0220824 A1 | | 10/2005 | Teckoe et al. |
| 2005/0233046 A1 | | 10/2005 | Krawczyk et al. |
| 2005/0233053 A1 | | 10/2005 | Shen et al. |
| 2005/0266116 A1 | | 12/2005 | Teckoe et al. |

FOREIGN PATENT DOCUMENTS

| | | |
|---|---|---|
| GB | 1 567 049 | 5/1980 |
| GB | 2395413 A1 | 5/2004 |
| JP | 08-151481 A2 | 6/1966 |
| JP | 9266779 | 10/1997 |
| JP | 10-056960 A | 3/1998 |
| JP | 11-046723 A2 | 2/1999 |
| JP | 11-299435 A2 | 11/1999 |
| JP | 2000-184853 A2 | 7/2000 |
| JP | 2001 190220 A | 7/2001 |
| JP | 2001-190222 A | 7/2001 |
| JP | 2002-125587 A | 5/2002 |
| JP | 2002345401 A1 | 12/2002 |
| JP | 2005-245217 A1 | 9/2005 |
| WO | WO 81-02521 A1 | 9/1981 |
| WO | WO 94/24888 A1 | 11/1994 |
| WO | WO 98/56826 | 12/1998 |
| WO | WO 00/04862 A2 | 2/2000 |
| WO | WO 01/32150 A1 | 5/2001 |
| WO | WO 0132152 A1 | 5/2001 |
| WO | WO 02/49451 A2 | 6/2002 |
| WO | WO 03/003843 A1 | 1/2003 |
| WO | WO 03/090558 A1 | 11/2003 |
| WO | WO 2005/030177 A2 | 4/2005 |

OTHER PUBLICATIONS

The Fitzpatrick Company Europe N.V., 'Introduction to Roll Compaction and the Fitzpatrick Chilsonator'. Mar. 1997.

Sheskey, P., et al. 'Roll Compaction Granulation of a Controlled-Release Matrix Tablet Formulation Containing HPMC'. Pharmaceutical Technology, Oct. 1999.

Zhang, Y., et al., 'Physical Properties and Compact Analysis of Commonly Used Direct Compression Binders'. AAPS Pharm. Sci. Tech. 4 (4) Article 62, Dec. 15, 2003.

Hsiu-O, H. et al., 'Characteristics of Codried Products of Microcrystalline Cellulose with Saccharides and Low-substituted Hydroxypropylcellulose'. Powder Technology, 127 2002, pp. 45-53.

Schroder, R. et al., 'Influence of Magnesium Stearate on the Compaction Behavior and Tablet characteristics of Co-Spray Dried Compounds vs Physical Blends'. Poster Presented at American Association of Pharmaceutical Science (Denver) Oct. 2001.

Jacob, S. et al. 'Novel Co-processed Excipients of Mannitol and Microcrystalline Cellulose for Preparing Fast DissolVing Tablets of Glipzide'. Indian Journal of Pharmaceutical Sciences, vol. 69 (5) Sep.-Oct. 2007, pp. 633-639.

Rowe, Sheskey & Weller, "Handbook of Pharmacuetical Excipients, Fourth Edition", 2003, Pharmaceutical Press, London. XP002281910, p. 110, col. 2.

Letter from India Patent Office Dated Nov. 10, 2010, Indian Patent Application No. 3514/DELNP/2004, 2 Pages.

Response filed by Remfry & Sagar, Dated Jul. 19, 2011, Re: Indian Patent Application No. 3514/DELNP/2004.

Letter from India Patent Office Dated Jan. 16, 2012; Sub: Hearing Notice in Reference of Application No. 3514/DELNP/2004, 1 Page.

E-Mail from Remfry & Sagar, Dated Feb. 21, 2012, Re: Indian Patent Application No. 3514/DELNP/2004, 7 Pages.

English Translation of the Amendment dated Nov. 11, 2010; JP 2004-504975.

English Translation of Argument dated Nov. 11, 2010; JP 2004-504975.

EngliSh Translation of the Amendment dated Nov. 16, 2009; JP 2004-504975.

English Translation of the Argument dated Nov. 16, 2009; JP 2004-504975.

Office Action dated Jun. 27, 2007; U.S. Appl. No. 10/513,530.
Reply filed Nov. 27, 2007; U.S. Appl. No. 10/513,530.
Office Action dated Feb. 22, 2008; U.S. Appl. No. 10/513,530.
Reply filed Apr. 25, 2008; U.S. Appl. No. 10/513,530.
Notice of Allowance dated Aug. 7, 2008; U.S. Appl. No. 10/513,530.
Supplemental Notice of Allowability dated Aug. 28, 2008; U.S. Appl. No. 10/513,530.
Communication Regarding Correction of Title; U.S. Appl. No. 10/513,530, Nov. 6, 2008.
Preliminary Amendment dated Jan. 26, 1999; U.S. Appl. No. 12/265,970.
Office Action dated Jun. 15, 1999; U.S. Appl. No. 12/265,970.
Amendment dated Sep. 15, 2009; U.S. Appl. No. 12/265,970.
Office Action dated Dec. 16, 2009; U.S. Appl. No. 12/265,970.
Amendment dated Feb. 22, 2010; U.S. Appl. No. 12/265,970.
Office Action dated Mar. 3, 2010; U.S. Appl. No. 12/265,970.
Office Action dated Jul. 19, 2010; U.S. Appl. No. 12/265,970.
Response filed Aug. 25, 2010, U.S. Appl. No. 12/265,970.
Notice of Allowance dated Sep. 9, 2010; U.S. Appl. No. 12/265,970.
Office Action dated Oct. 30, 2009 in CN Application No. 03814262.7.
English Translation of Response to an Office Action dated Oct. 30, 2009 filed in CN Application No. 03814262.7.

\* cited by examiner

MICROCRYSTALLINE CELLULOSE COMPOSITIONS

This application is a continuation of U.S. Ser. No. 12/265,970, filed Nov. 6, 2008, now U.S. Pat. No. 7,871,468; which is a continuation of U.S. Ser. No. 10/513,530, filed Aug. 31, 2005, now U.S. Pat. No. 7,462,232; which is a 371 filing of PCT/US03/15146, filed May 14, 2003; which claims benefit of US Provisional Application 60/380,398, filed May 14, 2002.

The present invention relates to microcrystalline cellulose compositions, to a process for their manufacture, and to products containing the same. More particularly the invention relates to particulate microcrystalline cellulose compositions having a mean particle size of less than about 10 microns and comprising closely bound microcrystalline cellulose and at least one hydrocolloid. The compositions are prepared by applying a shear force to a high solids mixture of microcrystalline cellulose and a hydrocolloid by vigorously kneading the mixture in the presence of an anti-slip agent.

BACKGROUND OF THE INVENTION

Microcrystalline cellulose (MCC) is a white, odorless, tasteless, relatively free flowing, crystalline powder that is virtually free from organic and inorganic contaminants. It is a purified, partially depolymerized cellulose obtained by subjecting alpha cellulose obtained as a pulp from fibrous plant material to hydrolytic degradation typically with mineral acid. It is a highly crystalline particulate cellulose consisting primarily of crystalline aggregates which are obtained by removing amorphous (fibrous cellulose) regions of a cellulosic material. MCC is used in a variety of applications including foods, pharmaceuticals and cosmetics.

Microcrystalline cellulose may be produced by treating a source of cellulose, preferably alpha cellulose in the form of pulp from fibrous plant materials, with a mineral acid, preferably hydrochloric acid. The acid selectively attacks the less ordered regions of the cellulose polymer chain thereby exposing and freeing the crystalline sites which form crystallite aggregates which constitute the microcrystalline cellulose. These are then separated from the reaction mixture, and washed to remove degraded by-products. The resulting wet mass, generally containing 40 to 60 percent moisture, is referred to in the art by several names, including hydrolyzed cellulose, hydrolyzed cellulose wetcake, level-off DP cellulose, microcrystalline cellulose wetcake or simply wetcake.

When the wetcake is dried and freed of water the resulting product, microcrystalline cellulose, is a white, odorless, tasteless, relatively free-flowing powder, insoluble in water, organic solvents, dilute alkalis and acids. For a description of microcrystalline cellulose and its manufacture see U.S. Pat. No. 2,978,446. The patent describes its use as a pharmaceutical excipient, particularly as a binder, disintegrant, flow aid, and/or filler for preparation of compressed pharmaceutical tablets.

Microcrystalline cellulose and/or hydrolyzed cellulose wetcake has been modified for other uses, notably for use as a gelling agent for food products, a thickener for food products, a fat substitute and/or non-caloric filler for various food products, as a suspension stabilizer and/or texturizer for food products, and as an emulsion stabilizer and suspending agent in pharmaceutical and cosmetic lotions and creams. Modification for such uses is carried out by subjecting micro-crystalline cellulose or wetcake to intense attrition forces as a result of which the crystallites are substantially subdivided to produce finely divided particles. However, as particle size is diminished, the individual particles tend to agglomerate or hornify upon drying, probably due to hydrogen or other bonding forces between the smaller sized particles. To prevent agglomeration or hornification, a protective colloid, such as sodium carboxy-methylcellulose (CMC), which wholly or partially neutralizes the bonding forces which cause agglomeration or hornification, may be added during attrition or following attrition but before drying. This additive also facilitates re-dispersion of the material following drying. The resulting material is frequently referred to as attrited microcrystalline cellulose or colloidal microcrystalline cellulose. For a description of colloidal microcrystalline cellulose, its manufacture and uses, see U.S. Pat. No. 3,539,365.

Colloidal microcrystalline cellulose is a white odorless, hygroscopic powder. On being dispersed in water, it forms white, opaque thixotropic gels with microcrystalline cellulose particles less than 1 micron in size. It is manufactured and sold by FMC Corporation (FMC) in various grades under the designations, among others, Avicel RC and Avicel CL, which comprise co-processed microcrystalline cellulose and carboxymethylcellulose sodium.

Recognizing the unacceptability of CMC in food ingredients in certain well-populated countries, McGinley in U.S. Pat. No. 4,263,334 avoids the use of CMC in a colloidal microcrystalline cellulose by using a combination of additives consisting of a first ingredient which is a carbohydrate sweetener, e.g., sucrose, dextrose, or hydrolyzed cereal solids, and a second ingredient which is a hydrocolloid, e.g., guar gum, locust bean gum, gum arabic, sodium alginate, propylene glycol alginate, carrageenan, gum karaya, or xanthan gum.

Another MCC-based stabilizing agent is described by Tuason et al. in U.S. Pat. No. 5,366,742. This agent is prepared by mixing colloidal MCC with sodium alginate in water and then adding a soluble calcium salt to the slurry in an amount which deposits a sodium, calcium alginate complex on the surface of the MCC to provide barrier coating properties. After homogenization, the slurry is spray dried. The resulting stabilizing agent may be redispersed in water by use of high shear methods which appear to break the calcium alginate crosslinks, thus allowing dispersion to occur. However, in order to disperse this stabilizing agent using minimal agitation, it is necessary to provide a calcium sequestrant to preferentially react with the calcium in the sodium, calcium complex, thereby solubilizing the alginate.

Not all hydrocolloids when coprocessed with MCC in accordance with prior art processes provide effective barrier coating properties to the spray-dried powder that is produced. In U.S. Pat. No. 5,192,569 McGinley et al. describe the coprocessing of MCC and a galactomannan gum, e.g., locust bean or guar gum. Prior to spray drying, the MCC is attrited and is, therefore, colloidal. However, the flocculated product is claimed to be comprised of spherical particles ranging in size from 0.1 to 100 microns. In Example 1 for instance, spray dried powder has a particle size range of 5-70 microns. Reconstitution or rehydration of this coprocessed material requires high shear conditions. In compositions having 15 weight % or more of the galactomannan gum, high shear dispersion of the spray-dried material results in fibrous particles. Either the spherical aggregates or the fibrous material is particularly effective in providing fat-like properties to foodstuffs.

U.S. Pat. No. 6,391,368 (Tuason et al.) discloses a composition comprising attrited colloidal microcrystalline wetcake which is coprocessed with iota carrageenan and dried. The composition is prepared by the following process:

(a) subjecting hydrolyzed cellulose alone to attrition to make colloidal microcrystalline cellulose;
(b) dispersing said colloidal microcrystalline cellulose in water heated to a temperature above the solubility temperature of the dry iota carrageenan to be coprocessed with said colloidal microcrystalline cellulose;
(c) adding the dry iota carrageenan to the heated dispersion of colloidal microcrystalline cellulose and mixing the components, creating a slurry;
(d) homogenizing said slurry; and
(e) drying said slurry to produce a coprocessed powder.

U.S. Pat. No. 6,037,380 (Venables et al) discloses a composition comprising microcrystalline cellulose, a relatively water insoluble attriting aid and, optionally a protective colloid. The compositions are prepared by the following process:
(a) blending together unattrited microcrystalline cellulose, an attriting agent which is relatively insoluble in water and optionally a protective colloid;
(b) subjecting the blend to high shear wet grinding for a time and under shear forces sufficient to reduce the particle size of the microcrystalline cellulose, and
(c) recovering the resulting ultra fine microcrystalline cellulose composition.

U.S. Pat. No. 6,117,474 (Kamada et al.) discloses a composition containing a fine cellulose and a water-insoluble calcium material. The compositions are prepared by cogrinding an aqueous suspension of cellulose particles and calcium particles. A water soluble gum and/or hydrophilic substance may be incorporated in order to prevent re-aggregation of the fine cellulose and water-insoluble calcium material upon drying.

U.S. Pat. No. 6,270,830 (Kamada et al.) discloses a stabilizer for meat products comprising fine cellulose and a gelling agent. The stabilizer may contain a potassium or calcium salt such as insoluble calcium carbonate, to control gelling.

SUMMARY OF THE INVENTION

In accordance with the present invention, a method has now been found for preparing a colloidal microcrystalline cellulose/hydrocolloid composition in which the hydrocolloid has a heterogeneous distribution of linkages and is more intimately mixed with and closely bound to the microcrystalline cellulose than has previously been possible. This result is accomplished by shearing a high solids mixture of the microcrystalline cellulose and the hydrocolloid by vigorously kneading in the presence of an anti-slip agent.

The composition of this invention may be the moist attrited microcrystalline cellulose/hydrocolloid solid recovered from the kneading process; or it may be the dried residue thereof prepared by removing moisture from the moist solid, the latter being preferred for storage, shipment and subsequent use in preparing microcrystalline cellulose based dispersions. The compositions have a mean particle size, when measured as described below, of less than about 10 microns.

DETAILED DESCRIPTION OF THE INVENTION

In accordance with the present invention improved compositions are provided comprising microcrystalline cellulose and a hydrocolloid. The compositions are prepared by (a) combining microcrystalline cellulose wetcake, a hydrocolloid and an anti-slip agent prior to uniform swelling of the hydrocolloid, and (b) shearing the combination.

The resulting compositions are characterized by a mean particle size smaller than has previously been achievable in MCC/hydrocolloid compositions and a unique particle size distribution depending upon the hydrocolloid(s) employed.

The Hydrocolloid

Any hydrocolloid that will impart an increased surface charge when used in combination with microcrystalline cellulose to produce colloidal microcrystalline cellulose compared to colloidal microcrystalline cellulose alone may be employed in the compositions of the present invention. These hydrocolloids include: seaweed polysaccharides such as carrageenan, agar, furcellaran, alginate and alginate derivatives such as propylene glycol alginate and monovalent salts of alginates such as the potassium and sodium salts, plant gums including galactomannans such as guar, locust bean gum, and tara; carboxymethyl guar, carboxymethyl locust bean gum; glucomannans such as konjac; tamarind seed; polysaccharide; pectin; karaya; acacia; tragacanth; bacterial polysaccharides such as xanthan and pullulan; gellan and wellan; cellulose gums; alkyl cellulose ethers including hydroxypropylmethyl cellulose, hydroxyethyl cellulose, hydroxymethyl cellulose and hydroxypropyl cellulose; and mixtures thereof. The carrageenans may include mu, kappa, kappa-2, nu, iota, lambda, theta and mixtures thereof. The carrageenan may be processed with no, low, or high levels of alkali. The carrageen may include refined, semi-refined, or unrefined grades and mixtures thereof. Preferred hydrocolloids include alginates and carrageenans. Of these, iota carrageenan and sodium alginate are especially preferred. Blends of hydrocolloids may be employed particularly blends of iota carrageenan or sodium alginate and a minor portion of other hydrocolloids such as xanthan or pectic substances so long as the anti-slip agent can interact sufficiently to retard hydration of the hydrocolloid blend in the presence of the microcrystalline cellulose wetcake to enable sufficient mechanical energy transfer under shearing to produce the co-attrited colloidal MCC/hydrocolloid.

Preferred results are achieved with natural hydrocolloids As used herein "natural" means present in or produced by nature and includes hydrocolloids recovered from a biological source such as plants or bacteria or microbial fermentation.

The Microcrystalline Cellulose

Any microcrystalline cellulose may be employed in the compositions of the present invention. Suitable feedstocks include, for example, wood pulp such as bleached sulfite and sulfate pulps, corn husks, bagasse, straw, cotton, cotton linters, flax, kemp, ramie, fermented cellulose, etc.

The amounts of microcrystalline cellulose and hydrocolloid may be varied over a wide range depending upon the properties desired in the final composition. For most applications the ratio should be equal to from 50/50 to 90/10 more preferably from 70/30 to 85/15 parts by weight.

The Anti-Slip Agent

The anti-slip agent is a non-lubricant material which functions in combination with the hydrocolloid. The anti-slip agent is employed in an amount sufficient to reduce slippage of the product admixture in the work zones of the equipment during processing, ie. between the rotating screw elements as well as between the extruder screw elements and the extruder barrel itself in a twin screw extruder during mechanical processing of the admixture.

For use in the present invention the anti-slip agent may be any inorganic salt which is essentially completely soluble in water. Aqueous soluble inorganic salts which may be used include, for example, sodium chloride, potassium chloride, calcium chloride, calcium lactate, calcium tartrate, calcium citrate, calcium monophosphate and magnesium chloride. Of these divalent salts are preferred. Calcium chloride is especially preferred.

The amount of inorganic salt depends upon the valency of the salt and the hydrocolloid involved. The minimum amount is that which is sufficient to produce a non-slippery environment with sufficient friction to transform the MCC aggregates into a colloidal form. If too much salt is used this results in too much friction, increasing the temperature thereby resulting in degradation of the hydrocolloid. In general an amount of from about 0.8% to about 3.0% by weight based on the total weight of solids may be used. In one embodiment which uses sodium alginate as the hydrocolloid and calcium chloride as the inorganic salt the amount of calcium chloride salt added is within the range 0.8% to 2.0% by weight preferably 1.0% to 1.5% for an 85:15 weight ratio of microcrystalline cellulose to alginate. In another embodiment which uses iota carrageenan as the hydrocolloid and calcium chloride as the inorganic salt, the added calcium chloride salt is within the range 1.0% to 3.0% by weight, preferably 2.0 to 2.5% for an 85:15 ratio of microcrystalline cellulose to carrageenan. Some amount of the salt generally remains in the final composition. When a divalent salt, such as calcium is used, the amount of divalent cation, CA++ is from about 0.18 to 3.5% based on the total weight of the powdered composition. This includes any amount of calcium ions associated with the hydrocolloid employed and may, therefore, be higher than the amount of ions in the anti-slip agent employed in the process. The amount of cation present is determined by the atomic absorption test method described below.

Process

In one embodiment the process of the present invention uses as the starting material a hydrolyzed microcrystalline cellulose wetcake which, as indicated above, contains 40-60% by weight water. The hydrocolloid in the form of a dry powder is added to the wetcake with mixing. Only a limited amount of water is available to wet, and swell, the hydrocolloid powder in the high solids mixture of microcrystalline cellulose wetcake and added hydrocolloid powder. After the hydrocolloid begins to hydrate—i.e., begins to wet and swell, a solution of the inorganic salt is added. It is an important aspect of the present invention that the salt addition occurs prior to uniform wetting and swelling of the hydrocolloid powder. However, the order of addition of the components is not narrowly critical and it is possible, for example, to add the inorganic salt solution to the MCC prior to addition of the hydrocolloid. In either case, the resulting combination is then subjected to a shear force (such as in a twin screw extruder) to vigorously knead the mixture and comminute the microcrystalline cellulose aggregates. As used herein shear force refers to an action resulting from applied force that causes or tends to cause two contiguous parts of a mixture to slide relative to each other in a direction generally parallel to their plane of contact. When sufficient salt has been added, the hydrocolloid microcrystalline cellulose mixture no longer responds in a slippery manner but is capable of transferring the shear force applied to the mixture as mechanical energy to communite the microcrystalline cellulose aggregates. The amount of force applied must be sufficient to force association between the microcrystalline cellulose particles and the hydrocolloid.

If insufficient salt is added, the mixture remains slippery and the shear force is primarily dissipated as mechanical energy by sliding action rather than transferred to comminute the microcrystalline cellulose aggregates. If too much salt is added, the resistance to shear is very high and the hydrocolloid in the mixture is subject to degradation due to localized heating.

The resulting sheared material is dispersed in water, homogenized and spray dried to produce the final composition of the present invention.

Most conveniently the present invention utilizes as one of the starting materials a hydrolyzed cellulose wetcake (i.e., the undried mass produced when a source of cellulose, preferably alpha cellulose in the form of pulp from fibrous plant materials, has been treated with a mineral acid and then washed to remove the acid and by-products) generally containing about 40 to about 60 percent moisture to which a hydrocolloid is added. An anti-slip agent such as an aqueous solution of a soluble salt is added to the mixture of the microcrystalline cellulose wetcake and hydrocolloid before the hydrocolloid has had an opportunity to uniformly swell. The mixture of partially hydrated hydrocolloid and microcrystalline cellulose particles is then subjected to high solids shearing wherein the partially swollen hydrocolloid facilitates attrition of the microcrystalline cellulose to provide colloidal particles. If the hydrocolloid were allowed to uniformly swell prior to shearing, the swollen hydrocolloid would be too slippery to be processed and there would be insufficient energy transfer during shearing to provide the necessary particle-to-particle abrasion forces required to reduce the microcrystalline particles to a consistent sub-micron size during the attrition step. In preparation of the wet blend, the moisture content may be adjusted as desired to produce the consistency desired for attrition of the blend and adjusted as needed during attrition to maintain the desired consistency. In a preferred embodiment the moisture present in the wetcake is generally sufficient. The use of excess water is to be avoided as it will tend to reduce the particle-to-particle abrasion forces which are necessary to reduce the microcrystalline cellulose particles to a consistent sub-micron size.

The wet blend is then attrited preferably as a high-solids wet blend under high shear high solids mixing conditions, in which the microcrystalline cellulose is ground into ultra-fine sub-micron sized particles which on dispersion are colloidally stable. The colloidal stability is further facilitated by inclusion of the protective hydrocolloid.

The protective hydrocolloids may perform one or more of several functions. They act as a barrier between and/or around the microcrystalline cellulose particles, presumably by attaching to or replacing the hydrogen bonding forces between them, and thus form a barrier between such particles to prevent them from hornifying. Secondly they act as dispersion aids to facilitate dispersion and rehydration of the microcrystalline cellulose particles when dried solid compositions of microcrystalline cellulose are redispersed. In addition, they may help in suspending and/or altering the rheological properties of the suspension.

Reduction of microcrystalline cellulose to colloidal particle size is preferably carried out by high solids, wet shearing of the blend of microcrystalline cellulose, inorganic salt solution and protective colloid. The use of a standard extruder, preferably with multiple screws, is a preferred means for reducing microcrystalline cellulose particle size. Other standard equipment may also be used for wet shearing operations, such as planetary mixers, for example Hobart mixers and roll mills, particularly those having three or more rolls. It is important that the equipment used provide high shearing action and provide intense rubbing, abrasive action on the microcrystalline cellulose, for example by forcing the mixture through passages of limited cross section such as those found in perforated plates of extruders and various other mixing equipment, or other passages of limited clearance such as between rolls of roller mills. The extrusion process is preferred for its ease of operation in high solids, high throughput processing and for its efficacy in yielding very fine particles of microcrystalline cellulose.

In the process of this invention, the first step comprises blending together unattrited microcrystalline cellulose and the hydrocolloid. The anti-slip agent is added prior to high shear kneading. As indicated above it is also possible to combine the microcrystalline cellulose and the anti-slip agent prior to addition of the hydrocolloid.

The wet blend is then subjected to high shear kneading for a time and under shear forces sufficient to reduce the microcrystalline cellulose to a particle size in which about 80% to 100%, advantageously about 90% to 100%, of the microcrystalline cellulose has a particle size not greater than 1 micrometer and is colloidally stable when dispersed in aqueous media. The hydrocolloid is closely bound to the microcrystalline cellulose.

The moist attrited microcrystalline cellulose composition resulting from the extrusion or other suitable kneading process may be recovered and then dispersed as a stabilizer/suspending agent for suspension and dispersions and/or may be further processed, dried and then dispersed for such uses. The further processing steps, if utilized, may involve preparing an initial dispersion, homogenizing the resulting dispersion, drying it, for example, by spray drying or other suitable means, all of which are within the skill of the art.

Depending on the starting ingredients and the ratios in which they are employed, compositions of this invention thus comprise an ultra-fine attrited microcrystalline cellulose composition comprising an anti-slip agent and microcrystalline cellulose particles which have a particle size as described above and a protective hydrocolloid, in which the weight ratio of microcrystalline cellulose to protective colloid is in the range of about 50:50 to about 90:10, preferably from 70:30 to 85:15.

The ultra fine colloidally stable microcrystalline cellulose/hydrocolloid product of this invention is utilized in dispersions, emulsions, suspensions and the like in an amount of from about 0.05-15 weight percent, advantageously 0.03 to 5 weight percent, preferably from about 0.05-3 weight percent, and is used as a filler or bulking agent, in an amount of about 1-15 weight percent, based on the final product. For food applications, 0.05-15 weight percent may suitably be used.

Composition

The products prepared by the present process differ from those prepared by prior art processes. As compared to the products prepared by the processes of the Kamada et al and Venables et al patents discussed above in which a solid attriting aid is used, the products of the present invention exhibit molecular distribution of the inorganic salt throughout the hydrocolloid/microcrystalline composition rather than in the form of fine inorganic particulates. The heterogeneous distribution of linked hydrocolloid closely bound with the colloidal microcrystalline cellulose provides for unique rheological behavior of the re-dispersed powder. As compared to the process of Tuason et al. discussed above in which the components of pre-attrited microcrystalline cellulose and sodium alginate are simply combined in a slurry, such that the alginate is uniformly hydrated when the soluble divalent metal salt is added, then subjected to high shear e.g., in a homogenizer, and dried to entrap the colloidal microcrystalline cellulose particles within a calcium alginate gel matrix, the products of the present invention exhibit finer colloidal particle size with tightly bound and heterogeneous linked alginate polymer due to high solids wet shearing of the microcrystalline cellulose wetcake and the partially swollen hydrocolloid in the presence of the antislip agent.

The compositions of the present invention are "coattrited" meaning that the MCC and the hydrocolloid are combined prior to application of high shear forces to the combination. They are characterized by physical properties not heretofore achievable.

All of the compositions contain at least 70% MCC and have a mean particle size of less than 10 microns. As used herein particle size refers to the value obtained by the test procedure described below. Preferred compositions have a particle size distribution (again determined by the test procedure described below) which depends on the hydrocolloid(s) used. Specifically, (i) when the hydrocolloid is a carrageenan at least about 50% of the particles have a particle size less than about 3.5 microns, (ii) when the hydrocolloid is a hydrocolloid other than a carrageenan at least about 30% of the particles have a particle size less than about 3.5 microns, and (iii) when the hydrocolloid is a combination of a carrageenan and another hydrocolloid at least about 20% of the particles have a particle size less than about 3.5 microns.

The products of the present invention can be used where colloidal grades of MCC are currently used including retortable chocolate beverages, bake stable bakery fillings, frozen desserts, aerated food systems, and salad dressings. These products are particularly suited for UHT-processed beverages, dairy and nondairy, such as those containing fresh soy protein or soy isolate, cocoa powder, and nutritional additives such as vitamins and minerals. In addition, this new colloidal MCC product extends product functionality to open up new opportunities for colloidal MCC. New product applications are due to the new and/or improved properties of the product. These include the following properties: reduced reactivity with proteins, improved freeze-thaw stability in low pH cultured dairy products, improved suspension functionality with wider process tolerance in UHT prepared beverages, improved texture modification in UHT cream products and improved heat stability in bakery fillings. Due to their reduced reactivity with proteins, the compositions can be used at low levels but with more process latitude since the range of effectiveness is broader so the amount is not narrowly critical. Dry mix products (instant sauces, gravies, soups, instant cocoa drinks, etc.), low pH dairy systems (sour cream/yogurt, yogurt drinks, stabilized frozen yogurt), baked goods (pie/pastry fillings), beverages (citrus flavored drinks, etc.), and products labeled all are areas of application. Other uses are as a bulking agent in non-aqueous food systems e.g., peanut butter, etc. and in low moisture food systems, as an excipient for chewable tablets, taste masking drug actives such as APAP, aspirin, ibuprofen, etc., suspending agent, and controlled release agent in pharmaceutical applications. These new colloidal products are also suitable for use as a delivery system for flavoring agents and nutraceutical ingredients in food, pharmaceutical and agricultural applications (including animal feed), and as a direct compression sustained release agent. They are also useful in pharmaceutical dosage forms such as tablets, films and suspensions. In addition they may be used as thickeners, in foams, creams and lotions for personal care (skin, hair) applications, and as suspending agents, for use with pigments and fillers in ceramics, colorants, cosmetics, and oral care and in industrial applications such as ceramics, delivery systems for pesticides including insecticides and in other agricultural products.

In order to illustrate the present invention the following examples are set forth.

In the Examples, the following standard materials and test procedures were used:

I. "Mean Particle Size" and Particle Size Distribution—

A dispersion was prepared with a Waring Blender (700 series), using a 1,000 ml bowl, at a speed of 18,000 to 19,000 rpm controlled by a Powerstat transformer which permits increasing of the Waring Blender speed gradually to avoid splashing.

1. Weigh 16 g (±0.01 g) of powder in a weigh boat.
2. Weigh 587±1 g distilled or deionized water in a 500 ml graduate and pour it into the blender bowl.
3. Slowly bring the blender speed up to about 30 volts with the transformer. Add the powder to the center of the water, taking care to prevent it from adhering to the sides of the bowl.
4. After the addition of the powder replace the bowl lid and mix for 15 seconds.
5. After 15 seconds mixing, increase the volts to 115, as quickly as possible, and mix at 115 volts for 2 minutes.
6. Store the dispersion in a 500 ml Nalgene bottle.

The mean particle size and the particle size distribution were measured using a Horiba LA-910 (available from Horiba Instruments, Inc., Irvine, Calif.) static light scattering particle size distribution analyzer.

II. Ca++ and Calcium Chloride Content—Measured by the Following Calcium Flame Atomic Absorption Test Method:

Procedure:

A. Standard/Blank Preparation:
1. Prepare a 5% lanthanum chloride solution as follows:
   Accurately weigh 12.5 g of lanthanum chloride 7-hydrate and transfer into a 250 mL volumetric flask containing approximately 100 mL of 0.1 N hydrochloric acid (HCl). Place in an ultrasonic bath for 10 minutes, remove and allow to cool to room temperature then fill to volume with 0.1 N HCl.
2. Prepare a 100-ppm calcium stock standard as follows:
   Transfer 10.0 mL of commercial 1,000-ppm calcium standard (Thermo Orion #922006, VWR #34183-182) into a 100 mL volumetric flask containing approximately 50 mL of 0.1NHCL, shake well and fill to volume with 0.1 N HCl.
3. Prepare 2, 4, 7, 10, 13 and 16-ppm calcium standards as follows:
   Transfer 2, 4, 7, 10, 13 and 16 mL of the 100-ppm calcium stock standard into labeled 100 mL volumetric flasks containing 10 mL of 5% lanthanum chloride solution and approximately 50 mL of 0.1 N HCl. Shake well and fill to volume with 0.1 N HCl.
4. Prepare a blank solution as follows:
   Transfer 10 mL of 5% lanthanum chloride solution into a 100 mL volumetric flask and fill to volume with 0.1 N HCl.

B. Sample Preparation:
1. Perform loss on drying (LOD) testing on all samples to determine percent moisture.
2. Transfer 200 mg of MCC sample into a labeled 100 mL volumetric flask with approximately 50 mL of 0.1 N HCl.
3. Place in an ultrasonic bath for 30 minutes, remove and allow to cool to room temperature.
4. Add 10 mL of 5% lanthanum chloride solution and fill to volume with 0.1 N HCl.
5. Centrifuge at 3,500 rpm/5 minutes and transfer supernatant into a 13×100 mm culture tube.
6. Dilute as necessary with 0.1 N HCl containing 0.5% lanthanum chloride to achieve results within the 2 to 16 ppm calcium range of the standard curve.

C. Analysis:
   Instrument: Perkin-Elmer Analyst 300 atomic absorption spectrometer.
   Lamp: Calcium
   Wavelength: 422.8 nm
   Signal Measurement Time Average
   Flame Type: Air/Acetylene
   Oxidant Flow: 10.0 L/min.
   Fuel Flow: 3.0 L/min
   Slit Width: 0.7
   Read Time: 5 seconds
   Delay Time: 28 seconds
   Calibration: Linear D. Calculation:

Weight of calcium (mg)=ppm calcium·100·Dilution Factor/1000% Calcium=(weight of calcium (mg)/sample weight (mg)·(100−% LOD/100))·100% Calcium chloride=% calcium·(110.98/40.08)

III. Bake (Heat) Stability—bake stability was determined by measuring shape retention by the following procedure. Shape retention is defined as the capacity of a fruit filling preparation to retain its initial shape and volume after being baked for a definite amount of time at a given temperature. A defined volume of fruit filling preparation (approx 35 g) is placed in a standardized ring (3.5 cm), which is placed on a paper graduated with concentric circles. The fruit filling is baked for a defined period of time at a specific temperature (usually 10 minutes at 400° F.) in a ventilated oven. After the heat treatment, the spread of the fruit filling is measured. The spread is expressed in a percentage [(Final diameter−initial diameter)/initial diameter×100].

Example I

In a 5 gal Hobart mixer, 1,744.9 grams of microcrystalline cellulose (MCC) wetcake with a solids content ranging from 38-44% was admixed with 90.8 grams of iota carrageenan to obtain an MCC to iota carrageenan solids ratio of 90/10 parts by weight. 27.7 grams of a 30% solution of $CaCl_2$ was added and mixed for several minutes. The admixture was passed through a co rotating twin-screw extruder several times to shear the admixture and comminute the microcrystalline aggregates. The resulting consistency of the extrudate was not slippery thereby enabling it to be subjected to a high work profile which facilitated the formation of colloidal microcrystalline cellulose particles.

418.6 grams of the MCC/iota carrageenan extrudate was dispersed in 2,581.4 grams of distilled water at about 160° F. The resulting slurry was passed through a Manton Gaulin homogenizer at 2,500 psi and spray dried to form a powder. The spray drying was performed as follows: The homogenized slurry was fed to a 3 foot (0.9144 m) Bowen spray dryer utilizing nozzle atomization 0.1 inch (0.00254 m) opening. The slurry was fed to the dryer by means of a variable feed Moyno pump at a rate to provide the desired outlet temperature. The operating inlet/outlet air temperature of the spray dryer was about 195° C./95° C. The spray drying conditions were regulated depending upon feed properties such as viscosity and resulting dried product characteristics and subsequent yield.

A water dispersible colloidal MCC powder having a very fine colloidal particle size distribution was obtained. Particle size analysis by laser light diffraction showed that the powder had a mean particle size of 5.33 microns and a particle size distribution of 85% of the particles less than 3.5 microns. When dispersed in deionized water, its 2.6% dispersion exhibited an initial Brookfield viscosity of 1,100 cps and a viscosity of 1,150 cps when retested after 24 hours.

COMPARATIVE EXAMPLE I

No Anti-Slip Agent

In a 5 gal Hobart mixer, 1,744.9 grams of microcrystalline cellulose (MCC) wetcake with a solids content ranging from 38-44% was admixed with 90.8 grams of iota carrageenan to obtain an MCC to iota carrageenan solids ratio of 90/10 parts by weight. The admixture was passed through a co rotating twin-screw extruder several times to shear the admixture and comminute the microcrystalline aggregates. The resulting consistency of the extrudate was very slippery and thus, the necessary friction or work profile in the extruder was not obtained to mechanically disintegrate the MCC aggregates to produce colloidal particles. Microscopic evaluation of the extrudate revealed that the MCC particles were large and unattrited thus, they were not colloidal.

EXAMPLE II

In a 5 gal Hobart mixer, 1,550.5 of microcrystalline cellulose (MCC) wetcake with a solids content ranging from 38-44% was admixed with 136.6 grams of iota carrageenan to obtain an MCC to iota carrageenan solids ratio of 85/15 parts by weight. 40 grams of a 30% solution of $CaCl_2$ was added and mixed for several minutes. The admixture was passed through a co rotating twin-screw extruder several times to shear the admixture and comminute the microcrystalline aggregates. The resulting consistency of the extrudate was not slippery thereby enabling it to be subjected to a high work profile which facilitated the formation of colloidal microcrystalline cellulose particles.

584.4 grams of the MCC/iota carrageenan extrudate was dispersed in 2,415.6 grams of distilled water at about 160° F. The resulting slurry was passed through a Manton Gaulin homogenizer at 2,500 psi and spray dried to form a powder. The spray drying was performed as follows: The homogenized slurry was fed to a 3 foot (0.9144 m) Bowen spray dryer utilizing nozzle atomization 0.1 inch (0.00254 m) opening. The slurry was fed to the dryer by means of a variable feed Moyno pump at a rate to provide the desired outlet temperature. The operating inlet/outlet air temperature of the spray dryer was about 195° C./95° C. The spray drying conditions were regulated depending upon feed properties such as viscosity and resulting dried product characteristics and subsequent yield.

A water dispersible colloidal MCC powder having a very fine colloidal particle size distribution was obtained. Particle size analysis by laser light diffraction showed that the powder had a mean particle size of 4.27 microns. When dispersed in water, its 2.6% dispersion exhibited an initial viscosity of 1,700 cps and a set-up viscosity of 2,450 cps when retested after 24 hours suggesting an effective interaction that is, a good gel network, between the MCC and the iota carrageenan.

A 0.5% level of this 85/15 microcrystalline cellulose/iota carrageenan provided a stable cocoa suspension in a retortable nutraceutical chocolate beverage and a UHT processed soy protein-based chocolate beverage.

COMPARATIVE EXAMPLE II

Insufficient Level of Anti-Slip Agent

In a 5 gal Hobart mixer, 1,539.3 grams of microcrystalline cellulose (MCC) wetcake with a solids content ranging from 38-44% was admixed with 127.6 grams of iota carrageenan to obtain an MCC to iota carrageenan solids ratio of 85/15 parts by weight. 25.0 grams of a 30% solution of $CaCl_2$ was added and mixed for several minutes. The admixture was passed through a co rotating twin-screw extruder several times to shear the admixture and comminute the microcrystalline aggregates. The resulting consistency of the extrudate was still slippery and thus, the necessary friction or work profile in the extruder was not obtained to mechanically disintegrate the MCC aggregates into ultra fine particles. Microscopic evaluation of the extrudate revealed that the MCC particles were large and unattrited thus, they were not colloidal. The amount of calcium salt added was insufficient to compete with the carrageenan for water hence, allowing the carrageenan gum to solvate further.

EXAMPLE III

In a 5 gal Hobart mixer, 1,915.3 grams of microcrystalline cellulose (MCC) wetcake with a solids content ranging from 38-44% was admixed with 387.1 grams of iota carrageenan to obtain an MCC to iota carrageenan solids ratio of 70/30 parts by weight. 75 grams of a 30% solution of $CaCl_2$ was added and mixed for several minutes. The admixture was passed through a co rotating twin-screw extruder several times to shear the admixture and comminute the microcrystalline aggregates. The resulting consistency of the extrudate was not slippery thereby enabling it to be subjected to a high work profile which facilitated the formation of colloidal microcrystalline cellulose particles.

309.3 grams of the MCC/iota carrageenan extrudate was dispersed in 2,690.7 grams of distilled water at about 160° F. The resulting slurry was passed through a Manton Gaulin homogenizer at 2,500 psi and spray dried to form a powder. The spray drying was performed as follows: The homogenized slurry was fed to a 3 foot (0.9144 m) Bowen spray dryer utilizing nozzle atomization 0.1 inch (0.00254 m) opening. The slurry was fed to the dryer by means of a variable feed Moyno pump at a rate to provide the desired outlet temperature. The operating inlet/outlet air temperature of the spray dryer was about 195° C./95° C. The spray drying conditions were regulated depending upon feed properties such as viscosity and resulting dried product characteristics and subsequent yield.

A water dispersible colloidal MCC powder having a very fine colloidal particle size distribution was obtained. When dispersed in water, its 2.6% dispersion exhibited an initial viscosity of 2,000 cps and a set up viscosity of 12,900 cps when retested after 24 hours suggesting an effective interaction that is, a good gel network between the MCC and the iota carrageenan.

A sweetened yogurt prepared using 0.25 wt % of this 70/30 microcrystalline celluose/iota carrageenan powder had a smooth consistency and glossy texture. When subjected to freeze/thaw conditions, the 70/30 MCC/iota-based product was stable as it maintained its smooth and glossy texture.

EXAMPLE IV

In a 5 gal Hobart mixer, 1,947.9 grams of microcrystalline cellulose (MCC) wetcake with a solids content ranging from 38-44% was admixed with 171.7 grams of sodium alginate to obtain an MCC to sodium alginate solids ratio of 85/15 parts by weight. 33.3 grams of a 30% solution of $CaCl_2$ was added and mixed for several minutes. The admixture was passed through a co rotating twin-screw extruder several times to shear the admixture and comminute the microcrystalline aggregates. The resulting consistency of the extrudate was not slippery thereby enabling it to be subjected to a high work profile which facilitated the formation of colloidal microcrystalline cellulose particles.

258.6 grams of the MCC/alginate extrudate was dispersed in 2,741.4 grams of distilled water at about 160° F. The resulting slurry was passed through a Manton Gaulin homogenizer at 2,500 psi and spray dried to form a powder. The spray drying was performed as follows: The homogenized slurry was fed to a 3 foot (0.9144 m) Bowen spray dryer utilizing nozzle atomization 0.1 inch (0.00254 m) opening. The slurry was fed to the dryer by means of a variable feed Moyno pump at a rate to provide the desired outlet temperature. The operating inlet/outlet air temperature of the spray dryer was about 195° C./95° C. The spray drying conditions were regulated depending upon feed properties such as viscosity and resulting dried product characteristics and subsequent yield.

A water dispersible colloidal MCC powder having a very fine colloidal particle size distribution was obtained. Particle size analysis by laser light diffraction showed that the powder had a mean particle size of 6.04 microns. When dispersed in water, its 2.6% dispersion exhibited an initial viscosity of 1,675 cps and a set up viscosity after 24 hours of 1,725 cps.

EXAMPLE V

85/15 MCC/A-H Kappa Carrageenan

In a 5 gal Hobart mixer, 1,938.1 grams of microcrystalline cellulose (MCC) wetcake with a solids content ranging 38-44% was admixed with 168.9 grams of fully modified calcium kappa carrageenan to obtain the desired MCC to kappa carrageenan solids ratio. 100 grams of a 15% solution of $CaCl_2$ was added and mixed for several minutes. The admixture was passed through a co rotating twin-screw extruder several times to shear the admixture and comminute the microcrystalline aggregates. The resulting consistency of the extrudate was not slippery thereby enabling it to be subjected to a high work profile which facilitated the formation of colloidal microcrystalline cellulose particles.

331.1 grams of the MCC/kappa carrageenan extrudate was dispersed in 2,268.9 grams of distilled water at about 160° F. 1.35 grams of $K_2CO_3$ was added and mixed for several minutes to adjust the pH to 8.0-8.5. The resulting slurry was passed through a Manton Gaulin homogenizer at 2,500 psi and spray dried to form a powder. The spray drying was performed as follows: The homogenized slurry was fed to a 3 foot (0.9144 m) Bowen spray dryer utilizing nozzle atomization 0.1 inch (0.00254 m) opening. The slurry was fed to the dryer by means of a variable feed Moyno pump at a rate to provide the desired outlet temperature. The operating inlet/outlet air temperature of the spray dryer was about 195° C./95° C. The spray drying conditions were regulated depending upon feed properties such as viscosity and resulting dried product characteristics and subsequent yield.

A water dispersible colloidal MCC powder having a very fine particle size distribution in which 50% of the particles were below 3.5 microns was obtained. When dispersed in water, its 2.6% dispersion exhibited an initial viscosity of 725 cps and a set-up viscosity of 3,350 cps.

In a UHT processed nutraceutical chocolate beverage application, the 85/15 MCC/kappa carrageenan used at 0.10% provided a stable cocoa suspension.

EXAMPLE VI

70/30 MCC/HM Pectin

In a 5 gal Hobart mixer, 1,676.5 of microcrystalline cellulose (MCC) wetcake with a solids content ranging 38-44% was admixed with 100 grams of a 30% solution of $CaCl_2$ and mixed for several minutes. 324.1 grams of high methoxyl (HM) pectin was added to obtain the desired MCC to HM pectin solids ratio. The admixture was passed through a co rotating twin-screw extruder several times to shear the admixture and comminute the microcrystalline aggregates. The resulting consistency of the extrudate was not slippery thereby enabling it to be subjected to a high work profile which facilitated the formation of colloidal microcrystalline cellulose particles.

315.1 grams of the MCC/iota carrageenan extrudate was dispersed in 2,684.9 grams of distilled water at about 160° F. 3 grams of $K_2CO_3$ was added and mixed for several minutes to adjust the pH to 5.0-5.4. The resulting slurry was passed through a Manton Gaulin homogenizer at 2,500 psi and spray dried to faun a powder. The spray drying was performed as follows: The homogenized slurry was fed to a 3 foot (0.9144 m) Bowen spray dryer utilizing nozzle atomization 0.1 inch (0.00254 m) opening. The slurry was fed to the dryer by means of a variable feed Moyno pump at a rate to provide the desired outlet temperature. The operating inlet/outlet air temperature of the spray dryer was about 195° C./95° C. The spray drying conditions were regulated depending upon feed properties such as viscosity and resulting dried product characteristics and subsequent yield.

A water dispersible colloidal MCC powder having a very fine particle size distribution was obtained. Particle size analysis by laser light diffraction of its 2.6% dispersion showed that it had a median particle size of 6.56 microns and a mean particle size of 8.98 microns. When dispersed in water, its 2.6% dispersion exhibited an initial viscosity of 675 cps and a set-up viscosity of 975 cps.

In a drinkable yogurt application, the 70/30 MCC/HM pectin used at 0.33% produced good stabilization.

EXAMPLE VII

70/30 MCC/PGA

In a 5 gal Hobart mixer, 1,089.8 grams of microcrystalline cellulose (MCC) wetcake with a solids content ranging 38-44% was admixed with 197.2 grams of propylene glycol alginate (PGA) with a high degree of esterification (DE) to obtain the desired MCC to PGA solids ratio. 65 grams of a 30% solution of $CaCl_2$ was added and mixed for several minutes. The admixture was passed through a co rotating twin-screw extruder several times to shear the admixture and comminute the microcrystalline aggregates. The resulting consistency of the extrudate was not slippery thereby enabling it to be subjected to a high work profile which facilitated the formation of colloidal microcrystalline cellulose particles. 312.0 grams of the MCC/PGA extrudate was dispersed in 2,688 grams of distilled water at about 160° F. The resulting slurry was passed through a Manton Gaulin homogenizer at 2,500 psi and spray dried to form a powder. The spray drying was performed as follows: The homogenized slurry was fed to a 3 foot (0.9144 m) Bowen spray dryer utilizing nozzle atomization 0.1 inch (0.00254 m) opening. The slurry was fed to the dryer by means of a variable feed Moyno pump at a rate to provide the desired outlet temperature. The operating inlet/outlet air temperature of the spray dryer was about 195° C./95° C. The spray drying conditions were regulated depending upon feed properties such as viscosity and resulting dried product characteristics and subsequent yield.

A water dispersible colloidal MCC powder having a very fine particle size distribution was obtained. Particle size analysis by laser light diffraction of its 2.6% dispersion showed that it had a median particle size of 5.87 microns and a mean particle size of 7.40 microns.

In a drinkable yogurt application, the 70/30 MCC/PGA used at 0.35% produced good stabilization.

EXAMPLE VIII

75/15/10 MCC/IOTA Carrageenan/HM Pectin

In a 5 gal Hobart mixer, 1,818.8 grams of microcrystalline cellulose (MCC) wetcake with a solids content ranging 38-44% was admixed with 163.7 grams of iota carrageenan to obtain the desired MCC to iota carrageenan solids ratio. 200 grams of a 15% solution of $CaCl_2$ was added and mixed for several minutes. The admixture was passed (1 pass) through a co rotating twin-screw extruder. 108 grams of high methoxyl (HM) pectin was added to the MCC/Iota carrageenan admixture. This was passed through the extruder several times to shear the admixture and comminute the microcrystalline aggregates. The resulting consistency of the extrudate was not slippery thereby enabling it to be subjected to a high work profile which facilitated the formation of colloidal microcrystalline cellulose particles.

343.6 grams of the MCC/iota carrageenan/HM pectin extrudate was dispersed in 2,656.4 grams of distilled water at about 160° F. The resulting slurry was passed through a Manton Gaulin homogenizer at 2,500 psi and spray dried to form a powder. The spray drying was performed as follows: The homogenized slurry was fed to a 3 foot (0.9144 m) Bowen spray dryer utilizing nozzle atomization 0.1 inch (0.00254 m) opening. The slurry was fed to the dryer by means of a variable feed Moyno pump at a rate to provide the desired outlet temperature. The operating inlet/outlet air temperature of the spray dryer was about 195° C./95° C. The spray drying conditions were regulated depending upon feed properties such as viscosity and resulting dried product characteristics and subsequent yield.

A water dispersible colloidal MCC powder having a very fine particle size distribution with 21% of the particles below 3.5 microns was obtained. When dispersed in water, its 2.6% dispersion exhibited an initial viscosity of 725 cps and a set-up viscosity of 925 cps.

In a sweetened yogurt product application, the 75/15/10 MCC/iota carrageenan/HM pectin used at 0.25% level produced a sweetened yogurt that had a smooth consistency and glossy texture. When subjected to freeze/thaw conditions, the MCC/iota carrageenan/HM pectin product was stable as it maintained its smooth and glossy texture

EXAMPLE IX 75/15/10 MCC/Iota Carrageenan/Xanthan Gum

In a 5 gal Hobart mixer, 1,818.8 grams of microcrystalline cellulose (MCC) wetcake with a solids content ranging 38-44% was admixed with 163.7 grams of iota carrageenan to obtain the desired MCC to iota carrageenan solids ratio. 200 grams of a 15% solution of $CaCl_2.2H_2O$ was added and mixed for several minutes. The admixture was passed (1 pass) through a co rotating twin-screw extruder. 107.2 grams of xanthan gum was added to the MCC/Iota carrageenan admixture. This was passed through the extruder several times to shear the admixture and comminute the microcrystalline aggregates. The resulting consistency of the extrudate was not slippery thereby enabling it to be subjected to a high work profile which facilitated the formation of colloidal microcrystalline cellulose particles.

343.5 grams of the MCC/iota carrageenan/HM pectin extrudate was dispersed in 2,656.6 grams of distilled water at about 160° F. The resulting slurry was passed through a Manton Gaulin homogenizer at 2,500 psi and spray dried to form a powder. The spray drying was performed as follows: The homogenized slurry was fed to a 3 foot (0.9144 m) Bowen spray dryer utilizing nozzle atomization 0.1 inch (0.00254 m) opening. The slurry was fed to the dryer by means of a variable feed Moyno pump at a rate to provide the desired outlet temperature. The operating inlet/outlet air temperature of the spray dryer was about 195° C./95° C. The spray drying conditions were regulated depending upon feed properties such as viscosity and resulting dried product characteristics and subsequent yield.

A water dispersible colloidal MCC powder having a very fine particle size distribution with 26% of the particles below 3.5 microns was obtained. When dispersed in water, its 2.6% dispersion exhibited an initial viscosity of 450 cps and a set-up viscosity of 700 cps.

EXAMPLE X

A fruit filling composition was prepared from the following components. All amounts are in parts by weight. In this Example, the following materials were used:
GRINSTED LA410—low ester amidated pectin available from Danisco.
COLFLO 67—modified cook-up starch from waxy maize available from National Starch.
Raspberry concentrate—20% fruit solids available from IFF.
MCC/Sodium Alginate—prepared as described in Example IV above.

| Component | Amount |
|---|---|
| GRINSTED LA410 | 5 |
| MCC/Sodium Alginate | 5 |
| Water | 420 |
| Sugar | 337 |
| COLFLO 67 starch | 20 |
| Raspberry concentrate | 200 |
| Potassium sorbate | 1 |
| 3% calcium lactate in water | 5 |
| 50% citric acid in water | 7 |
| Brix solids | 43% |
| Hot viscosity, cP | 13,800 |
| Bake stability | 11% |
| Gel strength, grams | 75 |

The GRINSTED LA410 and MCC/Sodium Alginate were dry blended and then dispersed in water using high shear mixing for 7 minutes. The sample was then heated to 90° C. while stirring. A dry blend of COLFLO 67 starch, sugar and potassium sorbate was added with stirring. After cooking for 10 minutes to ensure that the starch was dispersed, the Raspberry concentrate was added and the sample re-heated and held for 10 minutes at from 87° C. to 90° C. Brix was determined using a refractometer. The calcium lactate and citric acid solutions, were added sequentially. The fruit filling was poured into jars. Hot viscosity was measured using a Brookfield RVT #4 spindle, 10 rpm after 1 minute. The samples were cooled to room temperature and refrigerated prior to testing for gel strength and bake stability.

What is claimed is:

1. A coattrited composition consisting essentially of:
   (a) microcrystalline cellulose, and
   (b) a hydrocolloid,
   wherein (i) the composition has a mean particle size of more than 4.27 microns and less than about 10 microns; (ii) at least about 30% of the particles have a particle size less than about 3.5 microns, and (iii) said composition consists essentially of at least 70% by weight of said microcrystalline cellulose or the ratio of said microcrystalline cellulose to said hydrocolloid is equal to from 50/50 to 90/10, respectively.

2. A composition as claimed in claim 1 wherein the amount of hydrocolloid is equal to from 15% to 30% by weight based on the total weight of hydrocolloid and microcrystalline cellulose.

3. The composition of claim 1, wherein said microcrystalline cellulose is present in an amount of at least 70% by weight of said composition.

4. The composition of claim 1, wherein said ratio of said microcrystalline cellulose to said hydrocolloid is equal to from 50/50 to 90/10, respectively.

5. The composition of claim 1, wherein said composition consists of said microcrystalline cellulose and hydrocolloid.

6. The composition of claim 5, wherein said hydrocolloid consists of cellulose gum.

7. The composition of claim 1, wherein said composition has an initial viscosity of 2,000 cps and a set up viscosity of 12,900 cps after 24 hours when both are measured in a 2.6% water dispersion.

* * * * *